(12) United States Patent
Grant et al.

(10) Patent No.: US 7,441,123 B2
(45) Date of Patent: *Oct. 21, 2008

(54) METHOD AND APPARATUS FOR CHARACTERIZING AND ESTIMATING THE PARAMETERS OF HISTOLOGICAL AND PHYSIOLOGICAL BIOMETRIC MARKERS FOR AUTHENTICATION

(75) Inventors: J. Spencer Grant, Cedar City, UT (US); Rick V. Murakami, Nroth Ogden, UT (US); Clark Hinton, Glendale, AZ (US); Matthew W. Pettit, Mountain Green, UT (US)

(73) Assignee: Ensign Holdings, Salt Lake City, UT (US)

( * ) Notice: Subject to any disclaimer, the term of this patent is extended or adjusted under 35 U.S.C. 154(b) by 1713 days.

This patent is subject to a terminal disclaimer.

(21) Appl. No.: 09/815,885

(22) Filed: Mar. 23, 2001

(65) Prior Publication Data
US 2007/0016088 A1    Jan. 18, 2007

(51) Int. Cl.
    *G06K 9/00* (2006.01)
(52) U.S. Cl. .................. 713/186; 382/115; 600/508
(58) Field of Classification Search .................. 713/186; 382/115; 128/920, 923, 924; 600/508–509
See application file for complete search history.

(56) References Cited

U.S. PATENT DOCUMENTS

| | | | |
|---|---|---|---|
| 4,109,237 A | 8/1978 | Hill | 340/146.3 |
| 4,537,484 A | 8/1985 | Fowler et al. | 354/62 |
| 4,544,267 A | 10/1985 | Schiller | 356/71 |
| 4,582,985 A | 4/1986 | Lofberg | 235/380 |
| 4,614,861 A | 9/1986 | Pavlov et al. | 235/380 |
| 4,699,149 A | 10/1987 | Rice | 128/664 |
| 4,728,186 A | 3/1988 | Eguchi et al. | 356/71 |
| 4,742,458 A * | 5/1988 | Nathans et al. | 382/207 |
| 4,784,484 A | 11/1988 | Jensen | 356/71 |

(Continued)

FOREIGN PATENT DOCUMENTS

JP    SHO 60-126787    7/1985

(Continued)

OTHER PUBLICATIONS

Biel, L. et al. "ECG analysis: a new approach to human identification." IMTC/99. Proc. of the 16th IEEE Instrumentation and Measurment Technology Conf, vol. 1, pp. 567-661; 1999.*

(Continued)

Primary Examiner—Kennedy J Schaetzle
Assistant Examiner—Jessica Reidel
(74) Attorney, Agent, or Firm—John R. Thompson; Stoel Rives LLP

(57) ABSTRACT

A plurality of electronic signals corresponding to a histological and/or physiological marker, such as a heartbeat, are obtained, from an individual and are converted into electronic signal form. The signals are measured to obtain an actual measurement of a plurality of variable features of the electronic signals relating to the heartbeats. The measurements are mathematically analyzed to provide the probability of divergence of each actual measurement. Using the calculated probability of divergence, subsequent received waveforms measurements are analyzed for authentication purposes.

37 Claims, 6 Drawing Sheets

U.S. PATENT DOCUMENTS

| | | | | |
|---|---|---|---|---|
| 5,073,950 | A | 12/1991 | Colbert et al. | 382/2 |
| 5,077,803 | A | 12/1991 | Kato et al. | 382/4 |
| 5,088,817 | A | 2/1992 | Igaki et al. | 356/71 |
| 5,103,486 | A | 4/1992 | Grippi | 382/4 |
| 5,172,698 | A | 12/1992 | Stanko | 128/697 |
| 5,180,901 | A | 1/1993 | Hiramatsu | 235/380 |
| 5,230,025 | A | 7/1993 | Fishbine et al. | 382/4 |
| 5,335,288 | A | 8/1994 | Faulkner | 382/4 |
| 5,456,256 | A | 10/1995 | Schneider et al. | |
| 5,586,171 | A | 12/1996 | McAllister et al. | 379/67 |
| 5,623,552 | A | 4/1997 | Lane | 382/124 |
| 5,666,400 | A | 9/1997 | McAllister et al. | 379/67 |
| 5,704,352 | A | 1/1998 | Tremblay et al. | 128/630 |
| 5,719,950 | A | 2/1998 | Osten et al. | 382/115 |
| 5,737,439 | A | 4/1998 | Lapsley et al. | 382/115 |
| 5,774,571 | A | 6/1998 | Marshall | 382/119 |
| 5,787,185 | A * | 7/1998 | Clayden | 382/115 |
| 5,789,733 | A | 8/1998 | Jachimowicz et al. | 235/492 |
| 5,872,834 | A | 2/1999 | Teitelbaum | 379/93.03 |
| 5,982,914 | A | 11/1999 | Lee et al. | |
| 5,987,232 | A | 11/1999 | Tabuki | 395/187.01 |
| 6,088,585 | A | 7/2000 | Schmitt et al. | 455/411 |
| 6,104,913 | A | 8/2000 | McAllister | 455/41 |
| 6,104,922 | A | 8/2000 | Baumann | 455/410 |
| 6,148,094 | A | 11/2000 | Kinsella | 382/124 |
| 6,164,403 | A | 12/2000 | Wuidart | 180/287 |
| 6,171,112 | B1 | 1/2001 | Clark et al. | 434/322 |
| 6,182,892 | B1 | 2/2001 | Angelo et al. | 235/380 |
| 6,193,153 | B1 | 2/2001 | Lambert | 235/380 |
| 6,202,151 | B1 | 3/2001 | Musgrave et al. | 713/186 |
| 6,208,264 | B1 | 3/2001 | Bradney et al. | 340/825.31 |
| 6,225,890 | B1 | 5/2001 | Murphy | 340/426 |
| 6,232,874 | B1 | 5/2001 | Murphy | 340/426 |
| 6,269,348 | B1 | 7/2001 | Pare, Jr. et al. | 705/39 |
| 6,275,806 | B1 | 8/2001 | Pertrushin | 704/272 |
| 6,289,453 | B1 | 9/2001 | Walker et al. | 713/175 |
| 6,301,375 | B1 * | 10/2001 | Choi | 382/115 |
| 6,483,929 | B1 * | 11/2002 | Murakami et al. | 382/115 |
| 7,133,792 | B2 * | 11/2006 | Murakami et al. | 702/104 |
| 2001/0033220 | A1 * | 10/2001 | Stone et al. | 340/5.52 |
| 2002/0138768 | A1 * | 9/2002 | Murakami et al. | 713/202 |
| 2007/0063816 | A1 * | 3/2007 | Murakami et al. | 340/5.82 |

FOREIGN PATENT DOCUMENTS

| | | |
|---|---|---|
| JP | SHO 61-175865 | 8/1986 |
| JP | SHO 63-20583 | 1/1988 |
| JP | SHO 63-53099 | 3/1988 |
| JP | SHO 63-120385 | 5/1988 |
| JP | SHO 63-313288 | 12/1988 |
| JP | HEI 1-175362 | 12/1989 |
| JP | HEI 4-24889 | 1/1992 |
| JP | 2000-181871 | 6/2000 |
| WO | WO 88/04153 | 6/1988 |
| WO | WO 98/37519 | 8/1998 |

OTHER PUBLICATIONS

Office Action for U.S. Appl. No. 09/758,836, filed Jan. 10, 2001, mailed from the USPTO on Apr. 17, 2007, 12 pgs.
Office Action for U.S. Appl. No. 10/300,659, filed Nov. 19, 2002, mailed from USPTO on Dec. 27, 2007, 15 pgs.
Office Action for U.S. Appl. No. 09/758,836, filed Jan. 10, 2001, mailed from the USPTO on Jul. 23, 2008, 16 pgs.

* cited by examiner

TABLE A

| Features of Heartbeat Wave Form |
| --- |
| Rate of change (slope) at all locations of the wave form.<br>(There are n-1 of these per wave form. n= number of data points) |
| Shape of Peak associated with the strongest wave form feature |
| Shape of Peak associated with the dicrotic notch |
| Shape of Inverted Peak associated with dicrotic notch |
| Approach angle of Peak associated with the strongest wave form feature |
| Approach angle of Peak associated with the dicrotic notch |
| Approach angle of Inverted Peak associated with the strongest wave form feature |
| Approach angle of Inverted Peak associated with the dicrotic notch |
| Location of Peak associated with the strongest wave form feature |
| Relative location of Peak associated with the strongest wave form feature |
| Location of Peak associated with the dicrotic notch |
| Relative location of Peak associated with the dicrotic notch |
| Location of Inverted Peak associated with the dicrotic notch |
| Relative location of Inverted Peak associated with the dicrotic notch |
| Magnitude of Peak associated with the strongest wave form feature |
| Magnitude of Peak associated with dicrotic notch |
| Magnitude of Inverted Peak associated with dicrotic notch |
| Maximum rates of change along any defined segment of the wave form |
| Minimum rates of change along any defined segment of the wave form |
| Relative location associated with maximum rates of change along any defined segments of the wave form |
| Relative location associated with minimum rates of change along any defined segments of the wave form |
| Magnitude associated with maximum rates of change along a defined segment of the wave form |
| Magnitude associated with minimum rates of change along any defined segment of the wave form |
| Frequency of the wave form as determined by any data point |

FIG. 4

| Features of Heartbeat Wave Form |
| --- |
| Frequency of wave form as determined by a combination of data points |
| Trend measures associated with a feature |
| Trend measures associated with any segment and wave form |
| Cycles associated with any feature |
| Cycles associated with any segment of the wave form |
| Series associated with a feature |
| Series associated with a segment of the wave form |
| Variability estimates associated with features |
| Variability estimates associated with subsegments |
| Variability estimates associated with defined measures |
| Linear combination of features, segments, and data on a wave form |
| Non-linear combinations of features, segments, and data on a wave form |

FIG. 5

METHOD AND APPARATUS FOR CHARACTERIZING AND ESTIMATING THE PARAMETERS OF HISTOLOGICAL AND PHYSIOLOGICAL BIOMETRIC MARKERS FOR AUTHENTICATION

CROSS-REFERENCE TO RELATED APPLICATIONS

Not applicable.

STATEMENT REGARDING FEDERALLY SPONSORED RESEARCH OR DEVELOPMENT

Not applicable.

INCORPORATION-BY-REFERENCE OF MATERIAL SUBMITTED ON A COMPACT DISC

Not applicable.

BACKGROUND OF THE INVENTION

1. Field of the Invention

The present invention relates to a method and apparatus for characterizing and estimating the parameters of a person's heartbeat for the purpose of authenticating a biometric signal. More specifically, the present invention relates to methods and apparatus for characterizing and estimating the parameters of a heartbeat signal that is substantially unique to a person in order to permit the person to use the heartbeat signal as a biometric marker to activate a device, participate in a transaction, or identify him or herself.

2. Description of Related Art

The computer industry has recognized a growing need for sophisticated security systems for computer and electronic devices. The security systems are used to prevent unauthorized use and authenticate or identify individuals through electronic means. The biometric authentication industry has developed in response to this need. Biometrics is the measurement of quantifiable biological traits. Certain biological traits, such as the unique characteristics of each person's fingerprint, have been measured and compared and found to be unique or substantially unique for each person. These traits are referred to as biometric markers. The computer and electronics industry is developing identification and authentication means that measure and compare certain biometric markers with the intention of using the markers as biological "keys" or "passwords."

Biometric markers presently used by the industry for authentication and identification include the use of measurements of unique visible features such as fingerprints, hand and face geometry, and retinal and iris patterns, as well as the measurement of unique behavioral responses such as the recognition of vocal patterns and the analysis of hand movements. The use of each of these biometric markers requires a device to make the biological measurement and process it in electronic form. The device may measure and compare the unique spacing of the features of a person's face or hand and compare the measured value with a value stored in the device's memory. Where the values match, the person is identified or authorized.

Several types of technologies are used in biometric identification of superficial anatomical traits. For example, biometric fingerprint identification systems may require the individual being identified to place their finger on a visual scanner. The scanner reflects light off of the person's finger and records the way the light is reflected off of the ridges that make up the fingerprint. Hand and face identification systems use scanners or cameras to detect the relative anatomical structure and geometry of the person's face or hand. Different technologies are used for biometric authentication using the person's eye. For retinal scans, a person will place their eye close to or upon a retinal scanning device. The scanning device will scan the retina to form an electronic version of the unique blood vessel pattern in the retina. An iris scan records the unique contrasting patterns of a person's iris.

Other types of technologies are used for biometric identification of behavioral traits. Voice recognition systems generally use a telephone or microphone to record the voice pattern of the user received. Usually the user will repeat a standard phrase, and the device compares the measured voice pattern to a voice pattern stored in the system. Signature authentication is a more sophisticated approach to the universal use of signatures as authentication. Biometric signature verification not only makes a record of the pattern of the contact between the writing utensil and the recording device, but also measures and compares the speed of the writing and pressure applied in the process of writing.

Each of the prior art systems has a number of disadvantages. For example, fingerprint databases may raise significant privacy issues for those whose information is entered in the system. Hand and facial geometry recognition systems may require large scanners and/or expensive cameras. Voice recognition devices have problems screening out background noise. Signature recognition devices are subject to variations in the behavior of the individual. Retinal devices may require users to place their eye close to or on a scanning device, exposing the user to potential infection.

Another disadvantage of the prior art to biometric authentication is that there are only a limited number of biometric markers that are practical for implementing in computer and electronic devices. Biometric patterns used in the prior art to authenticate a person that are completely unique to each person may have only minute differences; the patterns that distinguish one person from another person may be subtle. Measuring and authenticating such patterns may require a high degree of electronic sophistication to read and differentiate between the various unique aspects of the biometric marker. If the biometric marker is used to identify an individual from a large group of individuals, the computer memory storage and processing capability may also have to be sophisticated, and therefore, may be expensive.

Another disadvantage of prior art is that with relatively few truly unique biometric markers, it is likely that use of those markers, such as a fingerprint, would be widespread. The widespread use of just one or two types of markers increases the likelihood that an unauthorized person could, by chance or otherwise, be improperly granted access. If an unauthorized person were improperly given access, that individual may have access to numerous secured devices or accounts. This is the same problem that exists when a person chooses the same password for all his accounts or electronic devices and the password is stolen.

U.S. Pat. No. 4,537,484 to Fowler et al. discloses a fingerprint imaging apparatus for use in an identity verification system. The system uses light, which is reflected off the finger through a system of mirrors to a linear photo diode ray. The fingers are rotated mechanically in order to scan the entire fingerprint.

U.S. Pat. No. 4,544,267 to Shore discloses an identification device that uses a beam of collimated light to scan the fingerprint. The light beam is then imaged onto a linear ray of photo-responsive devices. The information is processed to provide a set of signals containing fingerprint information.

U.S. Pat. No. 4,699,149 to Rice discloses a device for detecting the position of subcutaneous blood vessels such as by using the reflection of incident radiation off of a user's skin. The measured pattern is then compared with a previously determined pattern to verify the identity of the user.

U.S. Pat. No. 4,728,186 to Eguchi et al. discloses another method for detecting data points on uneven surface such as a finger, namely a fingerprint, using a light source illuminating the uneven surface through a transparent plate.

U.S. Pat. No. 4,784,484 to Jensen discloses an apparatus for automatic scanning of a fingerprint using an optical scanner. The user slides his finger across a scanning surface and an optical scanning system generates an electrical signal as a function of the movement of the finger across the optical scanning surface.

U.S. Pat. No. 5,073,950 to Colbert et al. discloses a method and apparatus for authenticating and verifying the identity of an individual based on the profile of a hand print using an optical scanner.

U.S. Pat. No. 5,077,803 to Kito et al. discloses a fingerprint collating system employing a biological detecting system.

U.S. Pat. No. 5,088,817 discloses an apparatus for detecting and identifying a biological object by projecting a light beam onto the object and detecting the reflective light using an optical detector. The change in the wave length characteristics of the light beam can be compared to a previously determined pattern.

U.S. Pat. No. 5,230,025 discloses a system for generating data characteristics of a rolled skin print using an optical device that can convert reflective light beams into an electronic signal and generate digital data representative of the image of the skin print.

U.S. Pat. No. 5,335,288 to Faulkner discloses a biometric measuring apparatus that uses silhouette and light images to measure a person's hand features. The features are converted to electronic data and stored and later compared for identification purposes.

Some biometric authentication systems combine biometric measurements with conditioned behavior such as signature writing styles and voice patterns or intonations. For example, U.S. Pat. No. 5,103,486 to Grippey discloses a signature verification system utilizing a hand held writing implement that produces data regarding a person's fingerprint pattern and their hand written signature.

Other biometric authentication systems include means for verifying physiological activity. These means for verifying physiological activity are primarily to prevent an unauthorized person from using dead tissues as a means for circumventing the authentication process. For example, U.S. Pat. No. 5,719,950 to Osten et al. discloses a personal biometric authentication system wherein inherently specific biometric parameters are measured and recognized and at least one non-specific biometric parameter is recognized and compared with physiological norms. Likewise, U.S. Pat. No. 5,727,439 to Lapsley et al. discloses an antifraud biometric scanner that determines whether blood flow is taking place in the object being scanned and whether such blood flow is consistent with that of a living human.

It would therefore be advantageous to provide a method and apparatus for biometric authentication and activation that does not exclusively rely upon the measurement of superficial anatomical structure and/or behavioral responses. It would also be advantageous to provide a biometric authentication system that is relatively inexpensive and portable. It would be a further advantage to provide a biometric authentication system that can use, but does not require, unique biometric markers. It would also be advantageous to provide a method and apparatus for biometric authentication that can use a single technology to measure multiple, varied biometric markers.

BRIEF SUMMARY OF THE INVENTION

The present invention provides a method and apparatus for identification and authentication using physiological and histological biometric markers. The biometric markers of the present invention are substantially unique to each person, but not necessarily totally unique. In order to accomplish the present invention, it may be necessary to characterize and estimate the parameters of the physiological/histological markers. Characterization and estimation of the parameters of the physiological/histological marker will be referred to hereinafter as "individualization" of the physiological/histological markers. The biometric markers of the present invention are not merely measurements of superficial anatomical structure or behavioral traits, but instead utilize or alternatively include measurements of physiological traits of the various systems of the human body and/or are histological traits associated with tissues of the human body, which are individualized to enhance the traits' capacity to function as a biometric marker.

The present invention also contemplates the use of individualized biometric markers that may not be representative of any particular traits in and of themselves, but are a composite of various individualized physiological and/or histological traits. While the biometric markers of the present invention may be entirely unique to each person, markers that are not entirely unique but that are substantially unique may be used in the individualization and subsequent authentication process. This is made possible, in part, by the individualization system enclosed. In using substantially unique biometric markers, the present invention also allows a wide variety of biometric characteristics to be employed in a relatively compact and inexpensive device. The present invention employs an individualization method for use with biological markers that are substantially unique that remain relatively consistent from measurement to measurement and that preferably are capable of being measured without physically invasive procedures.

The present invention provides an efficient method for employing internal biometric markers. These internal markers can easily be used in conjunction with other biometric techniques to improve the layering technique. The layering technique can enhance the security capabilities of the present invention. Layering is a technique, which employs the use of more than one biometric marker for authentication. For example, the method of the present invention works to greatly simplify the measurement and authentication process, thereby making it more practical to employ layering techniques.

The use of physiological and histological markers allows the devices in which such a biometric system is used to be both secure and readily manufactured and marketable. The simplicity of these devices is due in great measure to the method of individualization that allows the measured waveform to be converted into a biometric marker. Because of the variety of ways in which the physiological markers can be measured and individualized using the present invention, a variety of measurements can be taken in the system, allowing for greater flexibility and variability in the markers used and design of the device. Contrary to the current trend in the biometric industry, the present invention does not limit the types of markers used to superficial anatomical structure or complex behavioral activity, and thus both simplifies and expands the potential applications for internal marks.

Other physical traits can be used for biometric authentication in conjunction with the individualization of a heartbeat. Where a biometric marker is measured using a signal that passes through these tissues, the tissues may have characteristics that affect the resulting signal or waveform characteristics that are substantially unique to each person. In a preferred embodiment of the present invention, a heartbeat waveform is measured using a signal that passes through dermal and subdermal tissues and their associated vasculature and musculature. Through these tissues the heartbeat of the user is measured and then individualized. The present invention provides for the use of specific histological traits of various human tissues, such as epithelial tissue, connective tissue, muscle tissue, and nervous tissue.

For example, the depth of the various layers of epithelial tissue from a given point on the skin surface may be a substantially unique histological trait that can be used as a biometric marker in conjunction with an individualized heartbeat. The density of a particular kind of connective tissue, such as bone density, may be a substantially unique histological trait that can be employed in a biometric authentication system. Likewise, the light absorption characteristics of skin tissue could be a substantially unique histological trait.

In the same way that histological markers increase both the marketability and security of biometric systems, the physiologically based biometric markers of the present invention provide similar advantages. Specifically, when properly individualized, the heartbeat waveform provides physiological markers that do not require the scanning or mapping of anatomical structure. Neither do the heartbeat waveform markers require the analysis of volitional acts, as are required with voice or signature analysis. The heartbeat is a non-volitional, physiological process that occurs in the body. A physiological marker, such as a heartbeat waveform marker, could also include or be combined with other physiological processes. A heartbeat waveform marker could be associated with a physiological marker related to a different system, such as, the integumentary system, the skeletal system, the muscular system, the pulmonary system, the respiratory system, the circulatory system, the sensory system, the nervous system, the digestive system, the urinary system, the endocrine system, and/or the reproductive system. Included in the physiological biometric markers are those activities associated with the various physiological systems that occur automatically or, in other words, are non-volitional. All of these systems and related subsystems provide traits that can be measured in a variety of ways to provide additional substantially unique biometric markers for the present invention and may in some cases be individualized with the heartbeat markers.

Physiological and histological biometric markers, whether related to the heartbeat or not, may be measured in common units such as spacial measurements of length, area, and volume. Frequency is also another type of measurement that can be practically applied to histological and physiological biometric markers. However, the present invention provides for the monitoring of these biometric markers in a variety of other additional ways. The relative motion of particles and fluids can be measured in terms of velocity, acceleration, volumetric flow rate or angular velocity, and angular acceleration. Physical interaction such as force, surface tension, pressure, viscosity, work, and torque are other possible measurements.

The physiological and histological markers may also be based upon energy or heat related characteristics such as power, heat quantity, heat flux, volumetric heat release, heat transfer coefficient, heat capacity, and thermal conductivity. Likewise, measurements, such as electric quantity, electromotive force, electric field strength, electric resistance, and electrical capacities, could provide biometric markers, depending upon the tissue or physiological process being monitored. Magnetic related characteristics, such as magnetic flux, induce, magnetic permeability, magnetic flux density, magnetic field strength, and magneto-motive force could be used. Other potential measurements may include luminous flux, luminance, illumination, radio nucleotide activity, radioactivity, temperature, and absorbed dose and dose equivalent, and amount of substance (mole).

In one preferred embodiment, an infrared light transmitter transmits an IR signal into a person's finger when the finger is placed on the transmitter. The signal transmitter is activated and a signal is emitted from the signal transmitter and is transmitted into the dermal and subdermal tissues of the person's finger. The signal is partly absorbed and reflected by the dermal and subdermal tissues. The reflected signal is received by a signal receiver and transmitted through receiving wires to a chip where the received signal or features of the signal are individualized. The signal may then be sufficiently unique to act as a biometric identifier or may be analyzed to provide extracted features of the signal that can be used as a biometric marker such as a digital heartbeat waveform. The biometric identifier is then stored for future use in authenticating the person.

Individualizing of the captured signal is accomplished using the method of the present invention. The process of individualizing the signal typically comprises capturing and recording a number of signals, estimating particular univariate and multivariate features of the signals, individualizing the measurements of the features and calculating probabilities for measurements of the feature. More specifically, one embodiment of the present invention comprises the steps of recording and saving the signal, measuring particular features of the signal, calculating the average of each measured feature, subtracting each measurement from the average to yield a centroid value, then, dividing each centroid by the standard deviation as calculated using the individualization set, determining the probability of the resulting figure using a distribution calculation and comparing the probability to the minimum value established.

Correlations between features are also calculated and compared to a threshold value. Correlation values above a specified threshold then qualify the multivariate characteristic for inclusion in authentication. The multivariate parameters of centroid, standard deviation and covariance are used to calculate the multivariate probability for comparison to the minimum value established.

BRIEF DESCRIPTION OF THE SEVERAL VIEWS OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying drawings in which:

FIG. 4 is a table of heartbeat wave form features;

FIG. 5 is a table of heartbeat waveform features; and

DETAILED DESCRIPTION OF THE INVENTION

Figure 1:
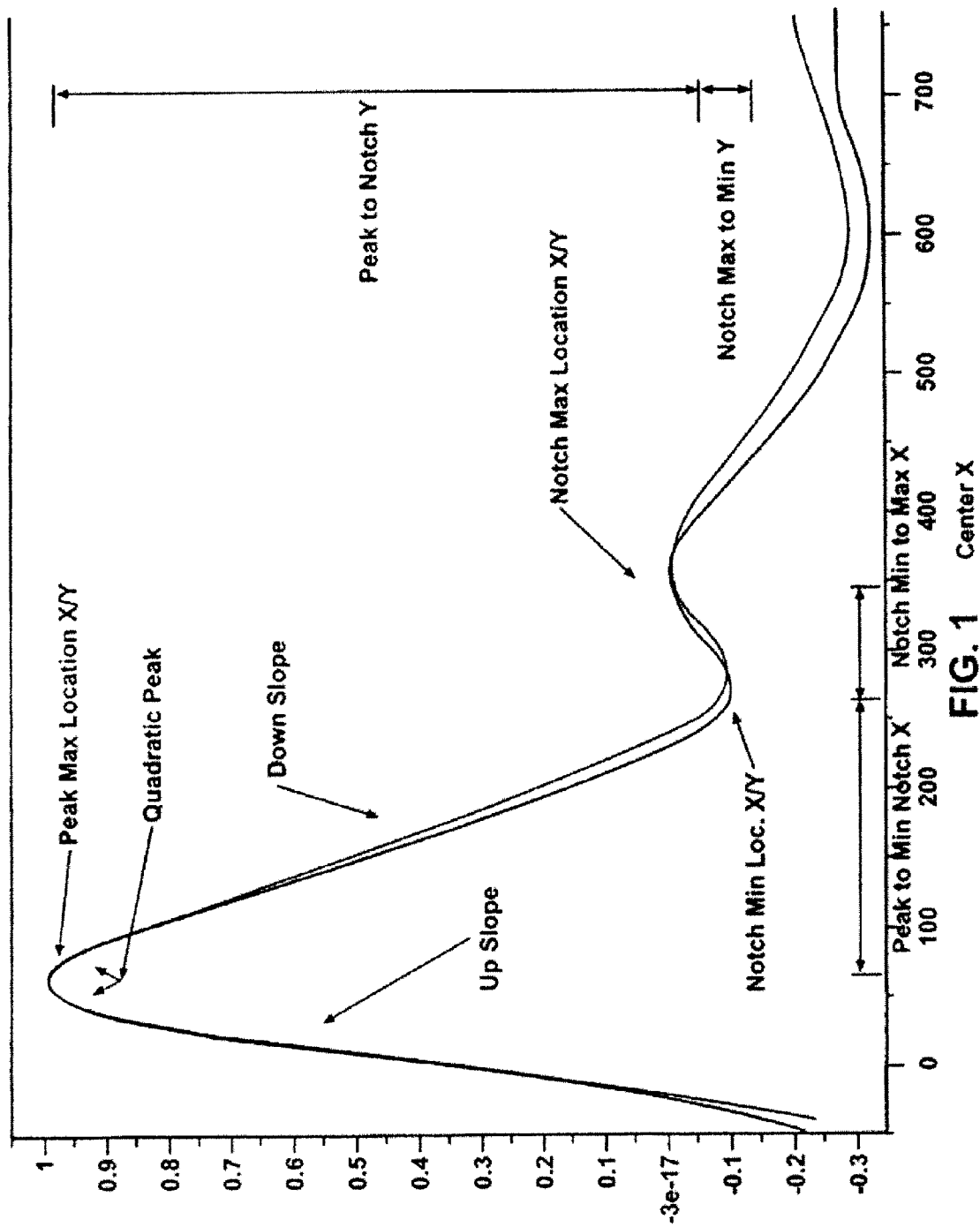
FIG. 1 illustrates various features of a waveform.
Figure 2:
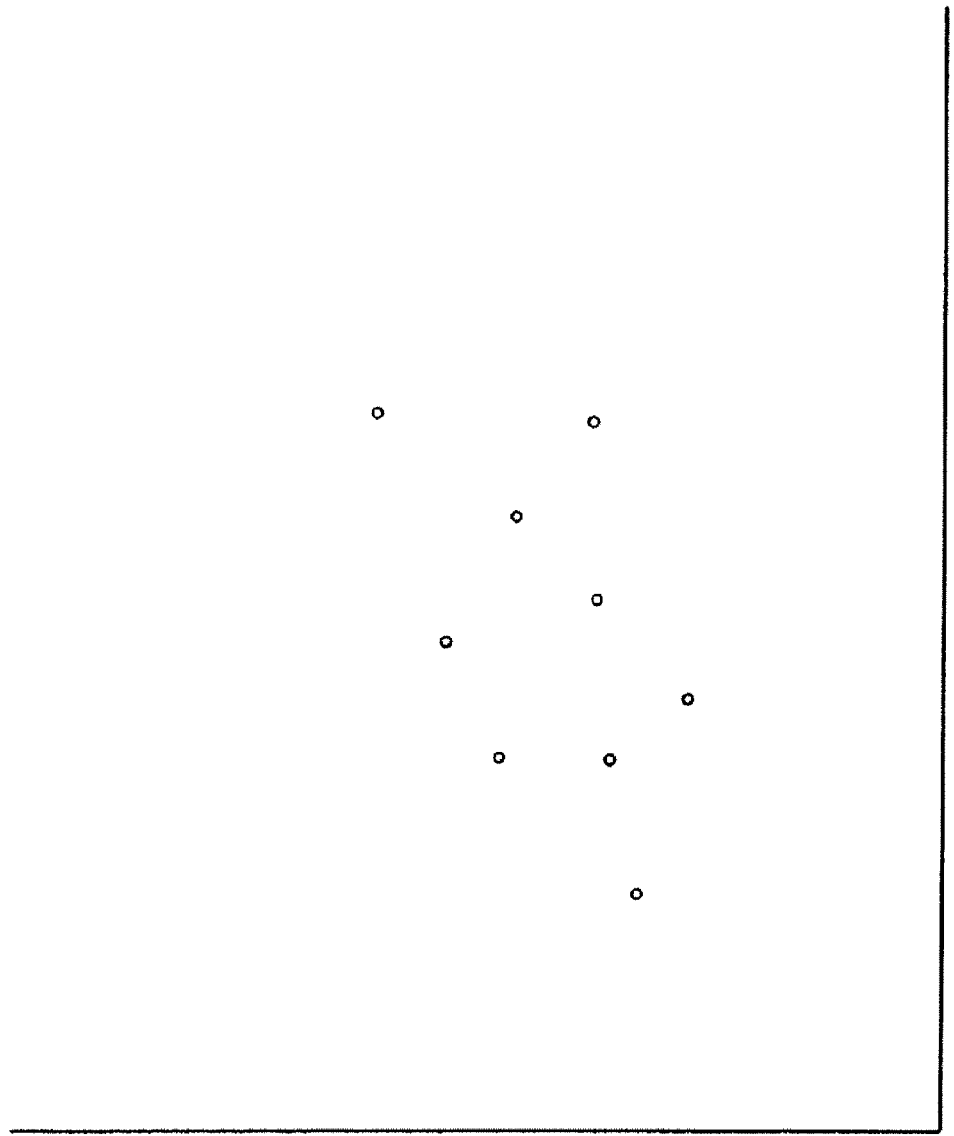
FIG. 2 illustrates a graph showing a strong bivariate relationship.
Figure 3:
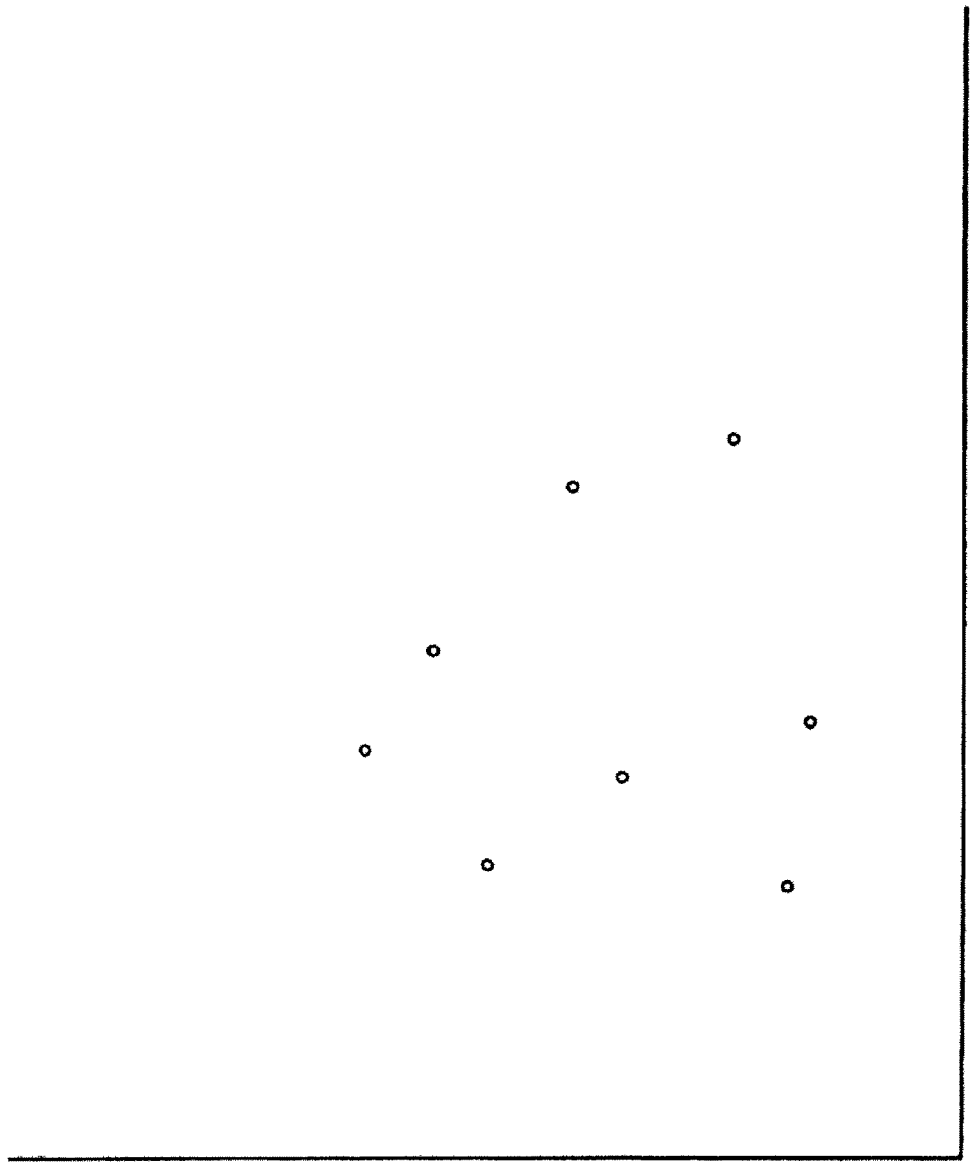
FIG. 3 illustrates a graph showing a weak bivariate relationship.

It will be readily understood that the components of the present invention, as generally described and illustrated in the figures herein, could be arranged and designed in a wide variety of different configurations. Thus, the following more detailed description of the embodiments of the system and method of the present invention, and represented in FIGS. 1 through 3, is not intended to limit the scope of the invention, as claimed, but is merely representative of the presently preferred embodiments of the invention. The presently preferred embodiments of the invention will be best understood by reference to the drawings.

The preferred embodiment of the present invention monitors the actual waveform of the heartbeat and retains certain features or attributes associated with that waveform for use in individualization and authentication. For example, the position on the upslope of the heartbeat waveform having the fastest rate of change slope can be recorded and various attributes of that position can be noted. The amplitude of that position, its position from the center of the pulse and amplitude of the actual beat relative to the position can all be measured and recorded. Thus, multiple quantitative features can be extracted from a single characteristic of a waveform.

All of the heartbeat waveforms share a number of standard features that can be used as reference points for other measurements. For example, all heartbeat waveforms can be divided into two distinct peaks. As part of the individualization process, the heartbeat waveform can be analyzed relative to the two peaks. Various parameters associated with waveform peaks include, but are not limited to, the differences between the two peak amplitudes, the differences between the two peak rate of changes, the relative position of the dicrotic notch, how deep the notch is, how far the dicrotic notch is from a zero point—a reference point, and how far it is from the center of one of the peak's, where the peak of the dicrotic notch is located along the horizontal, and the position of the various peaks from the center of the waveform and from the center of the other peak. Often several features can be extracted out of the waveform to serve in the individualization process.

In another example, shown in FIG. 1, various features of the waveform are monitored, such as peaks in the waveform, for quadratic and linear comparison. At the peak of the heartbeat, the waveform can be analyzed to show a quadratic fit. The quadratic term and the linear term of the quadratic that most closely correspond to the curve across the top of that heartbeat are potential features of the waveform that can be used for identification. Likewise, other features shown in FIG. 1 as well as those listed in Table A may prove useful in using the waveform as a biometric marker.

In a preferred embodiment, a total of 25 features are extracted out of a waveform to create a list of 25 parameters, each parameter representing a different unique feature for a particular person's heartbeat waveform. In addition to the selected heartbeat waveform parameters, other internal biometric features which are not related to a heartbeat waveform can be included in the list of parameters used in identification. For example, a measurement of the skin's light conductance may not be related to the heartbeat waveform and is a different kind of parameter, but light conductance can be easily measured in conjunction with the capture of the heartbeat waveform. These various features are ideally measured at the same time and can create very powerful identification multipliers since the features may vary over a wide range of individuals.

In order to individualize an internal biometric identifier such as a heartbeat waveform, the biometric must be read and recorded at least once. In order to assure an accurate biometric, it is preferable to take more than one reading of the biometric for purposes of individualization. In one preferred embodiment 30 heartbeats were taken and monitored to do the individualization for each person being identified. In another preferred embodiment, a hundred heartbeats were used. In capturing a good sample, it is preferred to take as many samples as is possible. However, taking a large number of sample waveforms takes time and using an extended period of time to individualize the waveform may be impractical.

Having collected various heartbeat waveforms from a person and determined various feature's measurements for each waveform, a table of extracted waveform features measurements can be created. The information in the table is used to individualize the waveforms of the person from whom the measurements were collected into a biometric authenticator.

The first step in the individualization process is determining the mean vector of the measured features in the table. For each feature on the table, the average of all the samples of that feature is calculated and then the average of that feature measurement is subtracted out from the actual measurement of the feature. The difference yields a value called the "centroid value" or "centroid vector" of the feature measurement.

Next, the standard deviation for each feature measurement is calculated, to show the degree statistical variation the waveforms have among themselves. Where there is little fluctuation or variation in a measured feature of the waveforms, the feature is relatively consistent and may be a good authenticating feature and the standard deviation is low. If there is significant variation in the waveform, the standard deviation is high.

Next, each of the measured features is subjected to a probability calculation. In one embodiment, using the centroidal information, the probability that a particular sample would exist given the range of measurements taken for that particular feature is determined. A valid sample is one that falls within a desired range of measurements. For any given sample, the probability calculation determines how closely that feature's measured value corresponds to the measurements of that same feature on other waveforms from that person. Where the measurements for the features of two waveforms are consistent and close together, the range of values for the measurement and related probabilities for the occurrence of that value can be determined. A subsequent measurement that shows up within that range of values that have a high probability of occurrence is a "valid" measurement. In other words, there is a good probability that the subsequently generated waveform could come from the person whose waveform generated the initial data set. In one preferred embodiment, the probability for each measurement is calculated using a T distribution and the centroid value and the standard deviation.

Before running the T-distribution, it is necessary to take into account the fact that for some of the features, the variation can be very rare, while for others, variations could be quite common. In order to individualize the values, the centroid value for each measurement is divided by the standard deviation. By individualizing of each one of the data samples, all the data samples will be in the same standard set regardless of the feature.

After the data are individualized, they are used to carry out the T distribution to generate corresponding probabilities for the measured values. Using these probability figures, a "threshold" value for each particular feature is determined, that is, the lowest acceptable probability value is determined. In one preferred embodiment the minimum univariate value is used as the threshold for determining whether the measurement taken of a particular feature is considered within the range of acceptable variance or is outside the acceptable range. The values calculated from an individual for whom the waveform is being individualized should fall above the minimum univariate value.

Obviously, it is possible that two people will have one or more waveform features so similar that the values taken from one will match or correspond to the other. If only one feature of the waveform were measured and individualized for the purposes of biometric authentication, then there is a strong possibility that two different people would have similar measured values for their "biometric profiles." In order to reduce the likelihood of such false positives, calculations are carried out for multiple features creating a table of univariates with corresponding minimum values. These minimum values can be compared or combined to yield an overall or global minimum univariate event called the total minimum.

The various data collected from the waveform and generated from the calculations performed on the collected waveform create a data set unique to person from whom the data were gathered. By combining the probabilities to create a univariate threshold, the present invention creates a unique biometric marker from a data set taken from an internal biometric marker.

In addition to univariate processing, the present invention also provides for bivariate processing. Bivariate processing begins with a determination of whether a relationship exists between the values for each of the features. For example, a determination must be made as to whether there is a correlation between feature one and feature two. If one feature represents amplitude of the waveform and a second feature is the amplitude of the dicrotic notch, and the two features measurements correspond in some reliable way, (e.g., the depth of the dicrotic notch is deep when the width of the pulse is narrow) the relationship can be used to further individualize the waveform to function as a biometric marker.

If there is a strong relationship between two univariate values, a linear correlation may exist and be used to individualize the waveform. The linear relation between the features can be shown graphically by taking the measured values and plotting it with the other related, measured values. Where the relationship between the values is strong, the graph has a cigar shape, as shown in FIG. 2, but where the relationship is not as strong, the graph would has a round shape instead, as shown in FIG. 3. In order to determine how well the features correlate with each other, each possible pairwise combination of features is evaluated. In the preferred embodiment having 25 features there are 300 possible bivariates. All 300 are analyzed for purposes of individualization.

In order to evaluate the degree of correspondence between two variables, the centroid value for each measurement of each measured feature is divided by its standard deviation and then multiplied together. The resulting values are summed and the summation is divided by the degrees of freedom (a value one less than the number of samples in the summation).

By comparing the bivariate combinations, a determination can be made as to which bivariates have the highest degree of correspondence. In some circumstances a user may have two different univariate values that individually are too inconsistent to function as validators, but show a strong correlation between their otherwise inconsistent values. These two "individually weak" univariates can be combined to form a strong bivariate. Using the summation calculation above, one can determine which bivariates have a strong correspondence. Bivariates that correspond exactly have a summation value of one. Where there is no correspondence at all, the summation value is zero. Bivariates with a correspondence close to one are typically the most helpful in individualizing the waveform and in subsequent authentication.

Having performed summation on a selected group of bivariates, a threshold value between zero and one is applied to the summation of the group. The selection of the threshold value is determined by balancing the need for highly correlating bivariates versus the need to employ a large number of bivariates. For example, a threshold value of 0.8 may be selected for a given group of bivariate. If the summation value of a particular bivanate is less than 0.8 then that bivanate value is not included in the biometric individualization, if it is above 0.8, then the bivariate correlates to an acceptable degree and the bivariate is included in the biometric individualization. Each one of these bivariates having a summation that falls above the 0.8 threshold value is electronically flagged and stored to be used as part of the individualization.

The number of bivariates that will be used in the individualization will depend upon the threshold values chosen and also on the individual for whom the individualization is done. Likewise the bivariates chosen will change from person to person because the bivariate correlation will change; some of the bivariates will work better for some people than they will for others. However, after the bivariates are established for a given person, the same bivariates are used for subsequent authentication.

Next the probability of the bivanates are calculated. In order to determine the probability that two bivanates properly authenticate the user, the Mahalanobis distance of the each of the bivariates is calculated. Determining this Mahalanobis distance involves calculating the average of the bivanates and determining the difference of each value from the average. Then using a cumulative gamma distribution calculation for each of the measured Mahalanobis distances, the probability that a certain bivariate represents the authentic user is calculated.

Comparing all of the univariate and bivariate probabilities, the minimum probability minimum value for all is obtained. The minimum probability can be used as threshold or basis for indicating identity between a present user's biometric "signature" and the signature as initially individualized. Alternatively, the probability value is just above the minimum value or some other probability value can be used.

All the information gathered and calculated by these various processes can be stored for use in individualization, calculations and verifications. The data is stored as the processes are completed. For example, for each feature, the measured value, the average, the centroid, the standard deviation, the minimum univariate T distribution, and the bivariates gamma distribution are stored in the device for later use.

In summary, the process of individualizing a person's heartbeat waveform under normal operations comprises the steps of capturing and saving the heartbeat signal, measuring particular features of the signal, subtracting each measurement from the average to yield the centroid, then, dividing each centroid by the standard deviation as calculated using the individualization set, determining the probability of the resulting figure using a distribution calculation and comparing the probability to the minimum value established. If the values are within the limits established by the individualization set, the person is authenticated. Using the data from the signal, a set of highly correlating bivariates is defined and distribution calculations are performed to determine the probability of the measured bivariates. The bivariate probabilities are also used in individualization and subsequent authentication.

One problem in making such authentication is knowing how to establish a minimum value for the univariate and bivariate values. In one alternative embodiment the minimum probability is used. However, in order to reduce the chances that an anomalous reading will be included in the individualization, a preferred embodiment uses a higher ordered minimum, such as a second or third ordered minimum. Naturally the higher up in this ordered sequence the minimum value is, the more likely the value will yield false negative.

In one embodiment of the present invention some of the features are globally weighted more than others during authentication. A particular feature, such as the slope of the dicrotic notch, may be considered more or less reliable as an identifier and thereby may be given more or less "statistical" weight in the individualization process. Likewise, the correlation between two measurements for a particular feature or the correlation between two different features may be stronger than for other features and be weighted accordingly. Some of the features may carry much more significant information than other features.

During the initial individualization process, it is preferable if the heartbeat signal captured is the first full heartbeat that occurs after the user has placed his finger on a device. The process preferably takes one second or less. In one embodiment, the biometric measuring hardware is primarily an analog circuitry and takes about one-half second before it is ready to begin sampling a user's heartbeat. Because of hardware limitations in some embodiments, heartbeat signal capture within two or more heartbeats is preferable.

The captured waveform is characterized and measured using various predetermined features of the waveform signal from an authenticated user. Based on these preselected features and parameters, individualization data sets are prepared, establishing parameters for each one of the features. The parameters for the features are then used to evaluate heartbeat signals during subsequent authentication. In other words, the present invention determines the likelihood or probability that a particular biometric waveform was generated by the authenticated user. Because the waveform measurements are never exactly the same from sample to sample, the present invention evaluates the probability that two waveforms come from the same person. For each authenticated waveform data sets, a threshold probability value is established for the purposes of authenticating the signal and for use of the signal as a biometric identifier. The threshold value is used to determine whether a specific user's waveform is considered authentic. The threshold may be any value that reflects the desired balance between consistency and selectivity.

One advantage of this embodiment of the present invention is that it takes into account that on occasion a typically consistent feature in a user's heartbeat waveform will be inconsistent with its usual pattern. The present invention is able to take such irregularities into account and still provide an authenticating process. For example, if a waveform has an abbreviated peak for some reason, that particular feature that represented the crown of the peak could be lost or unavailable for purposes of authentication. However, with the waveform individualized in accordance with the present invention, there are other features in the individualization set that are still reliable and those other features can accurately authenticate the user. An irregular feature may lower the probability of a positive authentication, but might not lower the probability to the point of giving a false negative. The user may be "recognized" and authenticated from the other features.

After individualization, it may be determined that some of the measured features of a user's waveform are not helpful in the identification process. In other words, for reasons of inconsistency or for other reasons some of the features may not provide information that can be included in individualizing the waveform. In one embodiment of the present invention, features which are not helpful in the individualization process are thereafter not determined or measured during any subsequent authentication procedures for that user. In another embodiment, the features are determined and measured but are not included in calculations or analysis of subsequent waveforms for authentication. By "turning off" the less helpful features, the biometric marker is more succinctly defined. During authentication, the stored memory of a device contains the user's individualization waveform set and only evaluates those particular bivariate and those particular features. Likewise, in another embodiment, in a pre-selection process based upon the relative weights and probabilities of various univariates and bivariates, certain features are flagged as being features that most clearly authenticate an individual. The flagged features are used as the authenticating features for the individual.

In one example the device authenticates a user based upon the user's selecting a user name or identification that is associated with a particular individualized waveform. In particular, the user activates the device which then prompts the user to select from among several registered users, or asks the user to identify himself. The user enters some form of identification recognizable to the device, such as entering or selecting a name, social security number or password, and the device recalls from machine memory the individualized waveform associated with the identifying entry. The machine then takes the waveform of the user and compares it to the waveform recalled from memory. If the waveforms correspond appropriately, the user is authenticated.

Alternatively, a device may be designed to provide access to twenty authorized users. The twenty users would each go through the individualization process to determine their individual templates or waveforms and a chip inside the device would store the waveforms or a remote database could store it and the device could access the database. The device then reads the waveform of potential users and interrogates the chip to compare the new waveform to the twenty waveforms stored in the device. If there is a match, the user is granted access. By the same system, the device can determine and keep track of who has accessed the device.

If a particular feature does not match the individualization values, this lowers the probability of generating a true positive. However, for the particular value there is also a range of probable values and based on these calculated probabilities.

The method of the present invention is carried out by being programmed in machine readable instructions, such as is common with computer software, and implemented to act on a computer system. The machine readable instructions may be integrated into a memory chip, or may be stored as data on a portable storage medium such as a floppy disk or CD ROM. The method may likewise be carried out using a signal transmitted over a wired or wireless network where, the signal carries the machine readable instructions.

Figure 6A:
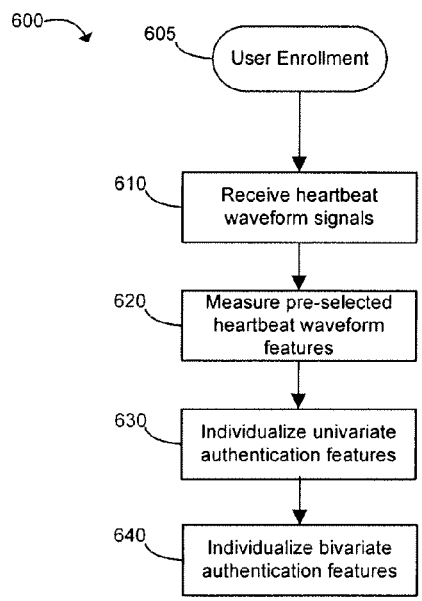
FIGS. 6a and 6b depict a flow diagram of a processing method for individualizing heartbeat waveform features of a user and using the individualized features to authenticate the user.
Figure 6B:
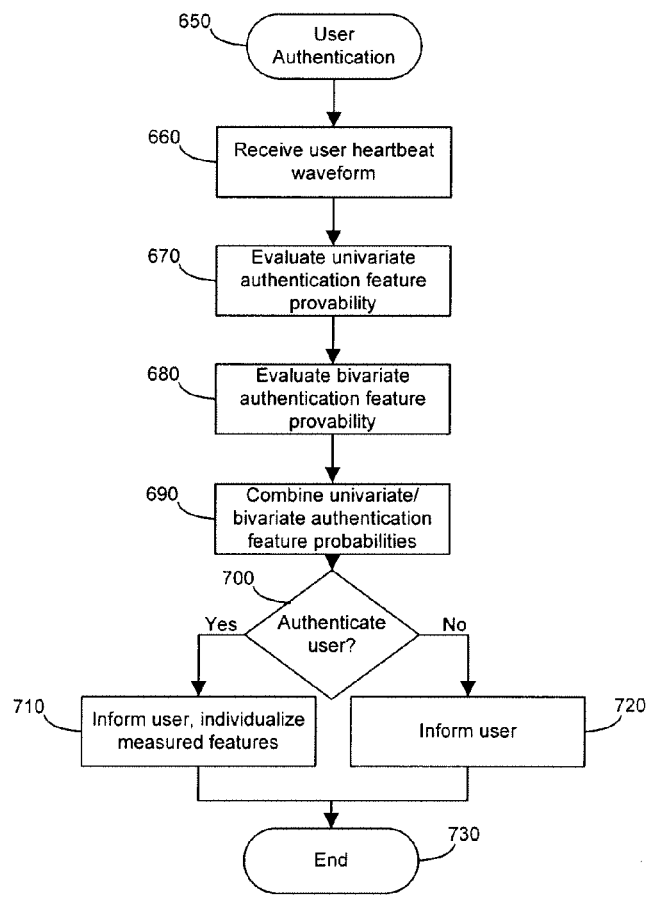

Referring now to FIGS. 6a and 6b, flow diagrams depict a processing methods 600 for individualizing heartbeat waveform features of a user and using the individualized features to authenticate the user. Processing methods 600 may be implemented on a computing system, and the method steps may be implemented as computer readable instructions stored on a computer readable storage media.

At step 605 the method may be initialized to enroll a new user. At step 610, a plurality of electronic signals corresponding to an internal biometric of an individual may be received. In embodiment 600, these electronic signals may correspond to a heartbeat waveform of an individual.

At step 620, one or more pre-selected heartbeat waveform features may be measured. The measured features may include, but are not limited to, the heartbeat waveform features listed in Table A of FIGS. 4 and 5.

At step 630, univariate authentication features of the received waveforms may be determined and individualized. In one embodiment, individualizing univariate features may comprise calculating statistical properties of the measured waveform features. First, an average or mean value of each feature measured at 620 may be calculated. This may be done by summing all of the feature measurements of 620 and dividing the result by the number of signals received at 610. After calculating the mean of each feature, a standard deviation value for the feature may be calculated. The standard deviation of a feature may show the degree of statistical variation of the feature among the waveforms received at 610. The standard deviation of a feature may be calculated by summing the squares of the difference between each feature measurement and the feature's mean and dividing the result by the number of waveforms received at 610.

The standard deviation value of each feature calculated may be used to determine whether a particular feature will be a good authenticator. For example, as discussed above, where there is little variation in a measured feature, the feature may be said to be relatively consistent and, as such, may be a good authentication feature. However, a large standard deviation in a feature may indicate that the feature is not consistent, indicating that the feature may be less effective for authentication. In one embodiment, method 600 may only use features having a standard deviation value below a pre-determined threshold.

The features measured at step 620 may then be "normalized" at step 630 by storing and associating the standard deviation with its corresponding feature. Then, when the feature is used to authenticate a user, the standard deviation value may be used to scale or weigh a particular feature measurement against its expected value. This may individualize each of the feature measurements into the same standard set regardless of the variation of the feature. This process may be considered as applying a "weight" to each feature depending upon the feature's deviation and/or effectiveness as an authenticator.

At step 640, bivariate features of the waveform signals received at 610 may be determined. As discussed above, bivariate features may be used as biometric authenticators. The process of identifying possible bivariate features may begin with a determination of whether a relationship exists between pairs of the features measured at step 620. For instance, a determination may be made as to whether there is a statistical correlation between the waveform amplitude feature and dicrotic notch amplitude feature. If there is a correlation, the relationship may be used as an authenticating feature of an individual's heartbeat waveform.

At step 640, the method may identify correlated features using linear correlation. A linear correlation may be shown graphically by taking the measured feature values and plotting them with the other, possibly related, feature values. Where the relationship between the variables is strong, the graph may take on a cigar shape as shown in FIG. 2. Where the relationship is not as strong, the graph may have a round shape as shown in FIG. 3. In order to evaluate the degree of correspondence between two variables, a centroid value for each feature measurement may be divided by its standard deviation and them multiplied together. As discussed above, a centroid value is the difference between a feature measurement and the mean value of the feature measurement. The resulting values may be summed together and divided by the degrees of freedom (the degrees of freedom is one less than the number of samples in the summation). As with univariate values, the degree of correspondence may act to weigh the relative efficacy of a particular bivariate for the purposes of authentication.

Although only bivariate feature correlations are discussed, it would be understood by one skilled in the art that any number of features could be combined to create other multivariate authenticators, such as trivariate, quadvariate, or the like.

At step 650, a user may be authenticated based on the individualized and weighted univariate and bivariate features determined at steps 605 and 640.

At step 460, a heartbeat waveform may be received from a user to be authenticated, and the heartbeat waveform features identified at and individualized at steps 620 to 640 may be measured.

At step 670, the features measured at 660 may be subjected to a univariate probability calculation to determine the probability that the features measured at 660 originated from the user. This probability may be calculated using a centroid value, standard deviation, and a T distribution. The centroid value of step 670 is calculated by taking a difference between the measurement of step 660 and the mean value for the feature (calculated at 630). The centroid may them be divided by the standard deviation for the feature (the weight of the feature) to "standardize" the feature relative to other features having greater or smaller standard deviation values. A T distribution may then be applied to generate a probability that the measured value corresponds to the individual enrolled at 605-640. The calculation of step 670 may be performed for all of the features measured at step 660 or for a sub-set of the features measured at step 660.

At step 680, each of the bivariate features, if any, determined and individualized at step 640 may be measured against the feature measurements of step 660 to determine bivariate probabilities. These probabilities may be calculated using a Mahalanobis distance between each of the bivariates. As discussed above, a Manalanobis distance may be calculated by calculating the average of the bivariates and determining the difference of each value from the average. The differences may be divided by the standard deviation of each bivariate (bivariate weight) in order to "standardize" the difference. The differences may then be applied to a cumulative gamma distribution resulting in a probability that the bivariate originated from a particular user. As in step 660, a probability may be calculated for each of the bivariate features individualized at step 640 for a sub-set of the bivariate features of step 640.

At step 690, the probabilities calculated for univariate features at steps 670 and bivariate features at step 680 may be combined to determine an overall probability that the waveform received at 660 was generated by the user enrolled and individualized at steps 605 to 640. This determination may be made on a feature-by-feature basis where the user may be rejected if any one univariate or bivariate feature diverges from the expected value by some threshold value or, alternatively, the determination may be based upon an overall probability. An overall probability may be determined by combining the probabilities calculated at steps 670 and 680 into a single value. The overall probably may then be compared against a threshold value to determine whether the user should be authenticated.

At step 700, the combined probability or probabilities determined at step 690 is compared against one or more threshold values. As discussed above, if the probability/probabilities are within a pre-determined threshold, the user may be authenticated. If not, the user may not be authenticated.

If the user is authenticated, the flow may continue to step 710. At step 710, the user may be informed that authentication was successful. In addition, the feature measurements obtained at step 660 may be included in individualization process of steps 630 and 640. In this way, the method may adapt to changes in the user's heartbeat waveform over time. The flow may then continue to step 730 where the method may terminate.

If the user was not authenticated, the flow may continue at step 720. At step 720, the user may be informed that authentication was not successful. The feature measurements obtained at step 660 should not be included in the individualization process if authentication fails. The flow may then continue to step 730 where the method may terminate.

What is claimed is:

1. A method in a computer system for individualizing a heartbeat signal for use as a biometric marker comprising the steps of:
   acquiring a plurality of electronic heartbeat signals from an individual in an electronic signal form using an optical sensor;
   for each electronic heartbeat signal, measuring, a plurality of pre-selected heartbeat waveform features to generate corresponding measurements;
   weighting the pre-selected heartbeat waveform features;
   providing a different statistical weight for each pre-selected heartbeat waveform feature; and
   authenticating an individual based on the weighted pre-selected heartbeat waveform features.

2. The method of claim 1 further comprising:
   for each electronic heartbeat signal, measuring an additional pre-selected heartbeat waveform feature to generate a corresponding additional measurement; and
   preventing the weighting of the additional pre-selected heartbeat waveform feature in the statistical analysis.

3. The method of claim 1 further comprising:
   individualizing the measurements of the pre-selected heartbeat waveform features; and
   calculating probabilities for the measurements.

4. The method of claim 3, wherein individualizing the measurements comprises:
   subtracting each corresponding measurement from an average value of the measurements to yield a centroid value for each pre-selected heartbeat waveform feature,
   dividing each centroid value by a standard deviation to yield a quotient value,
   determining a probability of the quotient value using a distribution calculation, and
   selecting a threshold minimum probability.

5. The method of claim 4, wherein calculating probabilities for the measurements comprises calculating a probability of divergence for each measurement using the quotient value.

6. The method of claim 5, wherein calculating the probability of divergence using the quotient value includes using the quotient value in a T-distribution analysis.

7. The method of claim 1, further comprising:
   calculating an average for each of said pre-selected heartbeat waveform features from said measurements;
   subtracting the average from each corresponding measurement to yield a centroid value;
   calculating a standard deviation for each pre-selected heartbeat waveform feature;
   dividing the corresponding centroid value by the standard deviation for each pre-selected heartbeat waveform feature; and
   calculating a probability of divergence for each measurement corresponding to each pre-selected heartbeat waveform feature.

8. The method of claim 7 further comprising:
   for each electronic heartbeat signal, measuring an additional pre-selected heartbeat waveform feature to generate a corresponding additional measurement; and
   preventing the weighting of the additional pre-selected heartbeat waveform feature in the statistical analysis.

9. The method of claim 1, wherein the pre-selected heartbeat waveform features include univariate features of a heartbeat waveform.

10. The method of claim 9, wherein the pre-selected heartbeat waveform features include multivariate features of a heartbeat waveform.

11. The method of claim 1, wherein a pre-selected heartbeat waveform feature is a position of a dicrotic notch.

12. The method of claim 1, wherein a pre-selected heartbeat waveform feature is a difference between two peak pressure amplitudes.

13. The method of claim 1, wherein a pre-selected heartbeat waveform feature is a difference between two peak pressure change rates.

14. The method of claim 1, wherein a pre-selected heartbeat waveform feature reflects how far a dicrotic notch is from a zero point.

15. The method of claim 1, wherein a pre-selected heartbeat waveform feature is an up slope of a maximum peak pressure.

16. The method of claim 1, wherein a pre-selected heartbeat waveform feature is a down slope of a maximum peak pressure.

17. The method of claim 1 further comprising:
   establishing a threshold probability value for each pre-selected heartbeat waveform feature, wherein the threshold value reflects a desired consistency and selectivity.

18. A computer readable storage medium containing instructions for controlling a computer system to perform a method to individualize a heartbeat electronic signal for use in biometric authentication, the method comprising:
   acquiring a plurality of electronic heartbeat signals from an individual in an electronic signal form using an optical sensor;
   for each electronic heartbeat signal, measuring one or more pre-selected heartbeat waveform features to generate corresponding measurements;
   weighing the pre-selected heartbeat waveform features;
   providing a different statistical weight for each of the one or more pre-selected heartbeat waveform features; and
   authenticating a user using said weighed pre-selected heartbeat waveform features.

19. The computer readable storage medium of claim 18 where said measurements are made on only one heartbeat waveform feature per acquisition.

20. The computer readable storage medium of claim 18 where said measurements are made on two heartbeat waveform features per acquisition.

21. The computer readable storage medium of claim 18 where said measurements are made on a plurality of heartbeat waveform features per acquisition.

22. The computer readable storage medium of claim 18, wherein said method further comprises:
    individualizing the measurements of the pre-selected heartbeat waveform features, and
    calculating probabilities for the measurements.

23. The computer readable storage medium of claim 22, wherein individualizing the measurements comprises:
    for each pre-selected heartbeat waveform feature, subtracting each corresponding measurement from an average value of the measurements to yield a centroid value,
    dividing each centroid value by a standard deviation to yield a quotient value,
    determining a probability of the quotient value using a distribution calculation, and
    selecting a threshold minimum probability.

24. The computer readable storage medium of claim 23, wherein calculating probabilities for the measurements comprises calculating a probability of divergence for each measurement using the quotient value.

25. The computer readable storage medium of claim 24, wherein calculating the probability of divergence using the quotient value includes using the quotient value in a T-distribution analysis.

26. The computer readable storage medium of claim 18, wherein said method further comprises:
    calculating an average for each of said pre-selected heartbeat waveform features from said measurements;
    subtracting the average from each corresponding measurement to yield a centroid value;
    calculating a standard deviation for each pre-selected heartbeat waveform feature;
    dividing the corresponding centroid value by the standard deviation for each pre-selected heartbeat waveform feature; and
    calculating a probability of divergence for each measurement corresponding to each pre-selected heartbeat waveform feature.

27. The computer readable storage medium of claim 18, wherein said method further comprises authenticating an individual based on the weighted pre-selected heartbeat waveform features.

28. The computer readable storage medium of claim 18, wherein the pre-selected heartbeat waveform features include univariate features of a heartbeat waveform.

29. The computer readable storage medium of claim 28, wherein the pre-selected heartbeat waveform features include multivariate features of a heartbeat waveform.

30. The computer readable storage medium of claim 18, wherein a pre-selected heartbeat waveform feature is a position of a dicrotic notch.

31. The computer readable storage medium of claim 18, wherein a pre-selected heartbeat waveform feature is a difference between two peak pressure amplitudes.

32. The computer readable storage medium of claim 18, wherein a pre-selected heartbeat waveform feature is a difference between two peak pressure change rates.

33. The computer readable storage medium of claim 18, wherein a pre-selected heartbeat waveform feature reflects how far a dicrotic notch is from a zero point.

34. The computer readable storage medium of claim 18, wherein a pre-selected heartbeat waveform feature is an up slope of a maximum peak pressure.

35. The computer readable storage medium of claim 18, wherein a pre-selected heartbeat waveform feature is a down slope of a maximum peak pressure.

36. The computer readable storage medium of claim 18, wherein said method further comprises:
    establishing a threshold probability value for each pre-selected heartbeat waveform feature, wherein the threshold value reflects a desired consistency and selectivity.

37. The computer readable storage medium of claim 18, wherein said method further comprises:
    measuring an additional pre-selected heartbeat waveform feature to generate a corresponding additional measurement for each electronic heartbeat signal; and
    preventing the weighting of the additional pre-selected heartbeat waveform feature in the statistical analysis.

* * * * *

UNITED STATES PATENT AND TRADEMARK OFFICE
CERTIFICATE OF CORRECTION

| | | |
|---|---|---|
| PATENT NO. | : 7,441,123 B2 | |
| APPLICATION NO. | : 09/815885 | |
| DATED | : October 21, 2008 | |
| INVENTOR(S) | : J. Spencer Grant et al. | |

It is certified that error appears in the above-identified patent and that said Letters Patent is hereby corrected as shown below:

On the Title Pg Item -56- Other Publications, Line 2, move the " to the end of Line 1.

On the Title Pg Item -56- Other Publications, Line 2 reads, "...Instrumentation and Measurment..." which should read, "...Instrumentation and Measurement..."

On the Title Pg Item -57- Abstract, Line 3 reads, "...are obtained, from..." which should read, "...are obtained from..."

Column 3, Line 9 reads, "...detecting data points on uneven surface..." which should read, "...detecting data points on an uneven surface..."

Column 7, Line 45 reads, "...from the center of one of the peak's..." which should read, "...from the center of one of the peaks..."

Column 8, Line 21 reads, "...determined various feature's measurements..." which should read, "...determined various features measurements..."

Column 8, Line 34 reads, "...to show the degree statistical variation..." which should read, "...to show the degree of statistical variation..."

Column 8, Line 55 reads, "...within that a range of values..." which should read, "...within that range of values..."

Column 9, Line 54 reads, "...the graph would has a round shape..." which should read, "...the graph has a round shape..."

Column 10, Line 20 reads, "...of a particular bivanate is less than 0.8 then that bivanate value..." which should read, "...of a particular bivariate is less than 0.8 then that bivariate value..."

Column 10, Line 21 reads, "...individualization, if it is above..." which should read, "...individualization; if it is above..."

UNITED STATES PATENT AND TRADEMARK OFFICE
CERTIFICATE OF CORRECTION

PATENT NO.         : 7,441,123 B2
APPLICATION NO. : 09/815885
DATED                 : October 21, 2008
INVENTOR(S)       : J. Spencer Grant et al.

It is certified that error appears in the above-identified patent and that said Letters Patent is hereby corrected as shown below:

Column 10, Line 36 reads, "...the probability of the bivantes are calculated." which should read, "...the probability of the bivariates is calculated."

Column 10, Line 37 reads, "...probability that two bivantes properly..." which should read, "...probability that two bivariates properly..."

Column 10, Line 38 reads, "...distance of the each..." which should read, "...distance of each..."

Column 10, Line 40 reads, "...calculating the average of the bivantes..." which should read, "...calculating the average of the bivariates..."

Column 10, Line 47 reads, "...the minimum probability minimum..." which should read, "the minimum probibility..."

Column 11, Line 50-51 reads, "...waveform data sets..." which should read, "waveform data set..."

Column 12, Line 21 reads, "...evaluates those particular bivariate..." which should read, "...evaluates those particular bivariates..."

Column 12, Line 55 reads, "...values and based on these..." which should read, "...values based on these..."

Column 12, Line 63 reads, "...wireless network where, the signal..." which should read, "...wireless network where the signal..."

Column 12, Line 66 reads, "...processing methods 600 for..." which should read, "processing method 600 for..."

Column 14, Line 6 reads, "...deviation and them multiplied together." which should read, "...deviation and then multiplied together."

Column 14, Line 34 reads, "The centroid may them be divided..." which should read, "The centroid may then be divided..."

UNITED STATES PATENT AND TRADEMARK OFFICE
CERTIFICATE OF CORRECTION

PATENT NO. : 7,441,123 B2
APPLICATION NO. : 09/815885
DATED : October 21, 2008
INVENTOR(S) : J. Spencer Grant et al.

It is certified that error appears in the above-identified patent and that said Letters Patent is hereby corrected as shown below:

Column 14, Line 60 reads, "...features at steps 670 and..." which should read, "...features at step 670 and..."

Column 15, Line 3 reads, "The overall probably may then be..." which should read, "The overall probability may then be..."

Column 15, Line 7 reads, "...probabilities determined at step 690 is compared..." which should read, "...probabilities determined at step 690 are compared..."

Column 15, Line 25 please insert the following paragraph, --The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.--

Column 15, Line 33 reads, "...for each electronic heartbeat signal, measuring, a plurality..." which should read, "for each electronic heartbeat signal, measuring a plurality..."

Signed and Sealed this

Twenty-third Day of June, 2009

JOHN DOLL
*Acting Director of the United States Patent and Trademark Office*